(12) United States Patent
Bernoud et al.

(10) Patent No.: US 11,571,372 B2
(45) Date of Patent: Feb. 7, 2023

(54) BRANCHED SATURATED HYDROCARBON COSMETIC INGREDIENT

(71) Applicant: BIOSYNTHIS, Saint Cyr Sous Dourdan (FR)

(72) Inventors: Thierry Bernoud, Saint Cyr Sous Dourdan (FR); Julien Magne, Roches-Premarie-Andille (FR); Antoine Piccirilli, Poitiers (FR)

(73) Assignee: BIOSYNTHIS, Saint Cyr Sous Dourdan (FR)

( * ) Notice: Subject to any disclaimer, the term of this patent is extended or adjusted under 35 U.S.C. 154(b) by 0 days.

(21) Appl. No.: 16/877,055

(22) Filed: May 18, 2020

(65) Prior Publication Data

US 2020/0383888 A1    Dec. 10, 2020

Related U.S. Application Data

(63) Continuation of application No. 15/762,415, filed as application No. PCT/EP2016/072621 on Sep. 22, 2016, now abandoned.

(30) Foreign Application Priority Data

Sep. 22, 2015    (FR) .................... 15/58954

(51) Int. Cl.
   *A61K 8/31*     (2006.01)
   *A61Q 19/00*    (2006.01)
   *A61Q 1/00*     (2006.01)

(52) U.S. Cl.
   CPC ............ *A61K 8/31* (2013.01); *A61Q 1/00* (2013.01); *A61Q 19/00* (2013.01); *A61K 2800/26* (2013.01)

(58) Field of Classification Search
   None
   See application file for complete search history.

(56) References Cited

U.S. PATENT DOCUMENTS

| | | | |
|---|---|---|---|
| 3,886,287 A | | 5/1975 | Kobayashi et al. |
| 4,026,960 A | | 5/1977 | Nishida et al. |
| 7,404,975 B2 | * | 7/2008 | Chen ............ A61K 36/185 424/774 |
| 2003/0181770 A1 | | 9/2003 | Both et al. |
| 2004/0037859 A1 | | 2/2004 | Cecchi et al. |
| 2007/0071705 A1 | * | 3/2007 | De Oliveira ......... A61K 47/10 424/70.13 |

FOREIGN PATENT DOCUMENTS

| DE | 1124300 A1 | 1/1993 |
|---|---|---|
| FR | 2235897 A1 | 1/1975 |
| FR | 2250512 A1 | 6/1975 |
| FR | 2250515 A1 | 6/1975 |
| JP | 2000-063254 A | 2/2000 |
| JP | 2008-037792 A | 2/2008 |
| WO | 2005/067892 A1 | 7/2005 |
| WO | 2006/014035 A1 | 2/2006 |
| WO | 2010/121591 A1 | 10/2010 |
| WO | 2012/059702 A1 | 5/2012 |
| WO | 2013/093411 A1 | 6/2013 |

OTHER PUBLICATIONS

Giruts et al. Petroleum Chemistry 2013 53(4):209-219 (Year: 2013).*
Krkošová et al. Petroleum and Coal 2007 49(3): 51-62 (Year: 2007).*
Cvačka et al. Journal of Chemical Ecology 2006 32(2):409-434 (Year: 2006).*
Feb. 1, 2017 International Search Report issued in International Patent Application No. PCT/EP2016/072621.
Rosaria Ciriminna et al. "Catalytic Hydrogenation of Squalene To Squalane". Organic Process Research & Development, 2014, vol. 18, No. 9, pp. 1110-1115.
Laura Gilbert et al. "Rheological and Textural Characterization of Cosmetic Emulsions Containing Natural and Synthetic Polymers: Relationships Between Both Data". Colloids and Surfaces A: Physicochem. Eng. Aspects, vol. 421, 2013, pp. 150-163.
Géraldine Savary et al. "Impact of Emollients on the Spreading Properties of Cosmetic Products: a Combined Sensory and Instrumental Characterization". Colloids and Surfaces B: Biointerfaces, vol. 102, 2013, pp. 371-378.
Laura Gilbert. "Physicochemical and Sensory Characterization of Cosmetic Ingredients: a Methodological Approach". Polymers, University of Havre, 2012.
Feb. 4, 2016 Search Report issued in French Patent Application No. 1558954.
Feb. 15, 2022 Office Action issued in Brazilian Patent Application No. BR112018005546-8.
Feb. 10, 2016 Office Action issued in French Patent Application No. FR1558954.
Feb. 15, 2017 International Search Report issued in International Patent Application No. PCT/EP2016/072621.
Jan. 4, 2018 International Preliminary Report on Patentability issued in International Patent Application No. PCT/EP2016/072621.

(Continued)

*Primary Examiner* — Melissa S Mercier
*Assistant Examiner* — Caralynne E Helm
(74) *Attorney, Agent, or Firm* — Oliff PLC (57) ABSTRACT

A cosmetic ingredient including at least one plant squalane and at least one mixture of C24 to C48 alkanes, in at least dimeric form, chosen amongst the alkanes of formula (I), where n is 1 or 0, $R_1$, $R'_1$, $R_2$, $R'_2$, $R_3$ and $R'_3$, which may be identical or different, are chosen amongst hydrogen atoms, methyl radicals, and linear C8 to C30 alkyl radicals, at least one of R1, R'1, R2, R'2, R3 and R'3 is chosen amongst the linear C8 to C30 alkyl radicals, and at least one and at most one of R1, R'1, R2, R'2, R3 and R'3 is a methyl radical. The mixture of C24 to C48 alkanes have a viscosity between 12 and 25 mm2/s at 40° C.

15 Claims, 4 Drawing Sheets

(56) References Cited

OTHER PUBLICATIONS

Jan. 14, 2019 Office Action issued in European Patent Application No. 16 770 494.9.
Nov. 18, 2019 Office Action issued in U.S. Appl. No. 15/762,415.
Mar. 3, 2020 Office Action issued in Indian Patent Application No. 201837013393.
Aug. 20, 2020 Office Action issued in Chinese Patent Application No. 201680062298.6.
Sep. 15, 2020 European Search Report issued in European Patent Application No. 20185582.
Oct. 7, 2020 Office Action issued in Japanese Patent Application No. 2018-515068.
Oct. 24, 2020 Office Action issued in Brazilian Patent Application No. BR112018005546-8.
Jun. 8, 2021 Office Action issued in Brazilian Patent Application No. BR112018005546-8.

\* cited by examiner

BRANCHED SATURATED HYDROCARBON COSMETIC INGREDIENT

This is a Continuation of application Ser. No. 15/762,415, filed Apr. 9, 2018, which is a National Phase of International Application No. PCT/EP2016/072621 filed Sep. 22, 2016, which claims the benefit of French Application No. 15/58954 filed Sep. 22, 2015. The disclosure of the prior applications is hereby incorporated by reference herein in its entirety.

BACKGROUND

Squalane ($C_{30}H_{62}$), obtained by hydrogenation of squalene ($C_{30}H_{50}$), is a cosmetic ingredient which is commonly used, in particular, for its very special sensory characteristics which it confers to the composition in which it is integrated, for its exceptional technical qualities in terms of formulation, and for its dermatological properties. Originally, it was obtained from squalene extracted from shark liver oil and then hydrogenated.

A plant squalane substitute has then been extracted from the olive oil, but this olive squalane suffers, in particular, from supply difficulties due to climate problems, diseases and parasites which are attacking olive trees all over the world. In 2014, for example, the European production dropped by 45% primarily due to climate problems. In 2015, the proliferation of *Xylella fastidiosa* results in a threat to Italian production . . . .

The wax elimination (winterization) and purification processes also result in losses of 10 to 20%.

In addition, the evolution of the olive oil refining methods and the use of high-temperature methods promote the formation of byproducts, such as isomers and cyclic products which result in variations in the quality of the squalenes extracted from olive oil.

Numerous substitute products have been sought in order to respond to the ever-increasing demand, and various substitutes of plant origin, for example, sugar cane, have been prepared. An example that is mentioned is a plant squalane referred to as the squalane "sugar squalane," which is obtained by the condensation of farnesene using fermentation methods; however, not all the properties, in particular the properties due to the minority constituents, namely the phytosterols and the plant waxes of olive squalane, are present.

Most of the substitutes synthesized to imitate the structure of squalane are alkanes comprising numerous branches and methyl or ethyl substituents resulting in the obligation to use syntheses that are impossible to implement starting from compounds of natural or plant origin. This is the case, in particular, of the compounds described in the U.S. Pat. No. 3,886,287 in the name of SHISEIDO which, while they meet the specifications pertaining to tolerance and have a high stability with respect to the action of the microorganism, are not comparable to squalane from a sensory standpoint.

Numerous other plant sources such as sunflower or rice wax are used on a regular basis, but the organoleptic or sensory properties of the olive squalane cannot be reproduced.

SUMMARY

Surprisingly, a cosmetic ingredient comprising at least one C24 to C48 alkane, in at least dimeric form, can advantageously be substituted for a plant squalane in cosmetic formulations, while preserving and even improving the sensory characteristics of said plant squalane.

In dimeric form is understood to mean a compound resulting from the combination (dimerization) of two molecules.

In addition, these features are achieved with alkanes that do not comprise many short-chain substituents, such as methyls or ethyls, and thus without trying to mimic the structure polysubstituted with methyl radicals of plant squalane.

In an embodiment, the plant squalane is an olive squalane.

The ingredient according to the invention, when added to the plant squalane, does not alter the properties of the plant squalane, and it can be added in proportions between 10 and 80%.

In an embodiment, it can be added in proportions between 10 and 50%.

Thus, the possibility exists of considerably decreasing the quantity of plant squalane without any negative consequence on the properties of the products which will be formulated.

The invention relates to a cosmetic ingredient comprising at least one plant squalane and at least one mixture of C24 to C48 alkanes, in at least dimeric form, chosen amongst the alkanes of formula I, Formula I wherein
n is equal to 1 or 0,
at least one of $R_1$, $R'_1$, $R_2$, $R'_2$, $R_3$ and $R'_3$, which may be identical or different, is chosen amongst the linear or branched C8 to C30 alkyl radicals,
and at most one of $R_1$, $R'_1$, $R_2$, $R'_2$, $R_3$ and $R'_3$ is a methyl radical, said mixture of C24 to C48 alkanes having a viscosity between 12 and 25 mm²/s at 40° C.

DETAILED DESCRIPTION

The invention relates to a cosmetic ingredient comprising at least one plant squalane and at least one mixture of C24 to C48 alkanes, in at least dimeric form, chosen amongst the alkanes of formula I, Formula I wherein
n is equal to 1 or 0,
at least one of $R_1$, $R'_1$, $R_2$, $R'_2$, $R_3$ and $R'_3$, which may be identical or different, is chosen amongst a group consisting of the linear or branched C8 to C30 alkyl radicals,
at least one of $R_1$, $R_2$ and $R_3$ is a hydrogen atom —H,
at least one of $R'_1$, $R'_2$ and $R'_3$ is a hydrogen atom —H,
and at most one of $R_1$, $R'_1$, $R_2$, $R'_2$, $R_3$ and $R'_3$ is a methyl radical, said mixture of C24 to C48 alkanes having a viscosity between 12 and 25 mm²/s at 40° C.

In an embodiment, at least one of $R_1$, $R'_1$, $R_2$, $R'_2$, $R_3$ and $R'_3$, which may be identical or different, is chosen amongst the linear C8 to C30 alkyl radicals. In an embodiment, $R_1$, $R'_1$, $R_2$, $R'_2$, $R_3$ and $R'_3$, which may be identical or different, are chosen amongst the group consisting of the hydrogen atoms —H, the methyl radicals and the linear or branched C8 to C30 alkyl radicals.

In an embodiment, $R_1$, $R'_1$, $R_2$, $R'_2$, $R_3$ and $R'_3$, which may be identical or different, are chosen amongst the group consisting of the hydrogen atoms —H, the methyl radicals and the linear C8 to C30 alkyl radicals.

In an embodiment, at least one of $R_1$, $R_2$ or $R_3$ and at least one of $R'_1$, $R'_2$ or $R'_3$ is a hydrogen atom.

In an embodiment, $R'_1$ is a methyl radical.

In an embodiment, $R'_1$ is a methyl radical, at least one of $R_1$, $R_2$ or $R_3$ and at least one of $R'2$ or $R'_3$ is a hydrogen atom —H.

In an embodiment, n=0, $R'_1$ is a methyl radical, R1, R2 and R'2 are hydrogen atoms —H, and R3 and R'3 are chosen amongst the linear or branched C8 to C30 alkyl radicals, and the alkanes of the at least one mixture of C24 to C48 alkanes, in at least dimeric form, are chosen amongst the alkanes of formula Ia.

Formula Ia

In an embodiment, n=0, R'$_1$ is a methyl radical, R1, R2 and R'2 are hydrogen atoms —H, and R3 and R'3 are chosen amongst the linear C8 to C30 alkyl radicals, and the alkanes of the at least one mixture of C24 to C48 alkanes, in at least dimeric form, are chosen amongst the alkanes of formula Ia.

In an embodiment, n=1, R'$_1$ is a methyl radical, R1 and R'2 are hydrogen atoms —H, and R2, R3 and R'3 are chosen amongst the linear or branched C8 to C30 alkyl radicals, and the alkanes of the at least one mixture of C24 to C48 alkanes, in at least dimeric form, are chosen amongst the alkanes of formula Ib.

Formula Ib

In an embodiment, n=1, R'$_1$ is a methyl radical, R1 and R'2 are hydrogen atoms —H, and R2, R3 and R'3 are chosen amongst the linear C8 to C30 alkyl radicals, and the alkanes of the at least one mixture of C24 to C48 alkanes, in at least dimeric form, are chosen amongst the alkanes of formula Ib.

In an embodiment, n=0, R1 and R'1 are hydrogen atoms —H, and R2, R'2, R3 and R'3 are chosen amongst the linear or branched C8 to C30 alkyl radicals, and the alkanes of the at least one mixture of C24 to C48 alkanes, in at least dimeric form, are chosen amongst the alkanes of formula Ic.

Formula Ic

In an embodiment, n=0, R1 and R'1 are hydrogen atoms —H, and R2, R'2, R3 and R'3 are chosen amongst the linear C8 to C30 alkyl radicals, and the alkanes of the at least one mixture of C24 to C48 alkanes, in at least dimeric form, are chosen amongst the alkanes of formula Ic.

In an embodiment, the branched alkanes of formula I, Ia, Ib and Ic are obtained by successive dimerizations of fatty alcohols originating from the catalytic hydrogenation of the coconut methyl esters, and comprise dimers, trimers, quadrimers or pentamers, followed by dehydration and hydrogenation.

In a preferred embodiment, the successive dimerizations are obtained by a Guerbet reaction.

In an embodiment, the fatty alcohols originating from the catalytic hydrogenation of the coconut methyl esters are dodecanol and decanol.

In an embodiment, the branched alkanes of formula I, Ia, Ib and Ic comprise 30 to 36 carbon atoms and consist primarily or dimers and trimers.

In an embodiment, the branched alkanes of formula I, Ia, Ib and Ic are obtained by successive dimerizations, by Guerbet reactions, of dodecanol and decanol, followed by dehydration and hydrogenation.

In an embodiment, the dimerization of decanol yields an octyldodecanol, which can then be dimerized with a dodecanol to yield a mixture of C32 isomers, consisting primarily of trimers. The medium can also comprise C24 dimers originating from the condensation of dodecanol with itself. The mixture is then subjected to a dehydration followed by a hydrogenation.

In an embodiment, the branched alkanes of formula I, Ia, Ib and Ic comprise at least one C30 trimeric alkane obtained by successive dimerizations of decanol.

In an embodiment, the branched alkanes of formula I, Ia, Ib and Ic comprise at least one C32 trimeric alkane obtained by successive dimerizations of decanol and dodecanol, followed by dehydration and hydrogenation.

In an embodiment, the branched alkanes of formula I, Ia, Ib and Ic comprise at least one C36 trimeric alkane obtained by successive dimerizations of dodecanol, followed by dehydration and hydrogenation.

In an embodiment, n is equal to 1.

In an embodiment, n is equal to 0.

In an embodiment, the alkyl radicals are chosen amongst linear C8 to C12 alkyl radicals.

In an embodiment, at least one of $R_1$, $R'_1$, $R_2$, $R'_2$, $R_3$ and $R'_3$ is a C8 alkyl radical.

In an embodiment, at least one of $R_1$, $R'_1$, $R_2$, $R'_2$, $R_3$ and $R'_3$ is a C9 alkyl radical.

In an embodiment, at least one of $R_1$, $R'_1$, $R_2$, $R'_2$, $R_3$ and $R'_3$ is a C10 alkyl radical.

In an embodiment, at least one of $R_1$, $R'_1$, $R_2$, $R'_2$, $R_3$ and $R'_3$ is a C11 alkyl radical.

In an embodiment, at least one of $R_1$, $R'_1$, $R_2$, $R'_2$, $R_3$ and $R'_3$ is a C12 alkyl radical.

In an embodiment, at least one of $R_1$, $R'_1$, $R_2$, $R'_2$, $R_3$ and $R'_3$ is a C13 alkyl radical.

In an embodiment, at least one of $R_1$, $R'_1$, $R_2$, $R'_2$, $R_3$ and $R'_3$ is a C14 alkyl radical.

In an embodiment, at least one of $R_1$, $R'_1$, $R_2$, $R'_2$, $R_3$ and $R'_3$ is a C15 alkyl radical.

In an embodiment, at least one of $R_1$, $R'_1$, $R_2$, $R'_2$, $R_3$ and $R'_3$ is a C16 alkyl radical.

In an embodiment, at least one of $R_1$, $R'_1$, $R_2$, $R'_2$, $R_3$ and $R'_3$ is a C17 alkyl radical.

In an embodiment, at least one of $R_1$, $R'_1$, $R_2$, $R'_2$, $R_3$ and $R'_3$ is a C18 alkyl radical.

In an embodiment, at least one of $R_1$, $R'_1$, $R_2$, $R'_2$, $R_3$ and $R'_3$ is a C19 alkyl radical.

In an embodiment, at least one of $R_1$, $R'_1$, $R_2$, $R'_2$, $R_3$ and $R'_3$ is a C20 alkyl radical.

In an embodiment, at least one of $R_1$, $R'_1$, $R_2$, $R'_2$, $R_3$ and $R'_3$ is a C21 alkyl radical.

In an embodiment, at least one of $R_1$, $R'_1$, $R_2$, $R'_2$, $R_3$ and $R'_3$ is a C22 alkyl radical.

In an embodiment, at least one of $R_1$, $R'_1$, $R_2$, $R'_2$, $R_3$ and $R'_3$ is a C23 alkyl radical.

In an embodiment, at least one of $R_1$, $R'_1$, $R_2$, $R'_2$, $R_3$ and $R'_3$ is a C24 alkyl radical.

In an embodiment, at least one of $R_1$, $R'_1$, $R_2$, $R'_2$, $R_3$ and $R'_3$ is a C25 alkyl radical.

In an embodiment, at least one of $R_1$, $R'_1$, $R_2$, $R'_2$, $R_3$ and $R'_3$ is a C26 alkyl radical.

In an embodiment, at least one of $R_1$, $R'_1$, $R_2$, $R'_2$, $R_3$ and $R'_3$ is a C27 alkyl radical.

In an embodiment, at least one of $R_1$, $R'_1$, $R_2$, $R'_2$, $R_3$ and $R'_3$ is a C28 alkyl radical.

In an embodiment, at least one of $R_1$, $R'_1$, $R_2$, $R'_2$, $R_3$ and $R'_3$ is a C29 alkyl radical.

In an embodiment, at least one of $R_1$, $R'_1$, $R_2$, $R'_2$, $R_3$ and $R'_3$ is a C30 alkyl radical.

In an embodiment, the C32 trimeric alkanes are obtained by the following reactions:

Step 1: Successive Dimerizations

Step 2: Dehydration

Step 3: Hydrogenation 11 12

-continued

In an embodiment, the C36 trimeric alkanes are obtained by the following reactions:
Step 1: Successive Dimerizations Step 2: Dehydration Step 3: hydrogenation In an embodiment, the cosmetic ingredient is characterized in that it comprises, in addition, at least one branched C24 to C48 alkane of general formula II, Formula II wherein
at least one of $R_1$, $R_2$ and $R_3$, which may be identical or different, is chosen amongst the linear or branched C8 to C30 alkyl radicals,
and at most one of $R_1$, R and $R_3$ is a hydrogen atom.

In an embodiment, at least one of $R_1$, $R_2$ and $R_3$, which may be identical or different, is chosen amongst the linear C8 to C30 alkyl radicals In an embodiment, the branched alkane comprises 28 to 36 carbons.

In an embodiment, none of $R_1$, $R_2$ and $R_3$ is a hydrogen atom.

In an embodiment, at least one of $R_1$, $R_2$ and $R_3$ is a hydrogen atom.

In an embodiment, at least one of $R_1$, $R_2$ and $R_3$ is a C8 alkyl radical.

In an embodiment, at least one of $R_1$, $R_2$ and $R_3$ is a C9 alkyl radical.

In an embodiment, at least one of $R_1$, $R_2$ and $R_3$ is a C10 alkyl radical.

In an embodiment, at least one of $R_1$, $R_2$ and $R_3$ is a C11 alkyl radical.

In an embodiment, at least one of $R_1$, $R_2$ and $R_3$ is a C12 alkyl radical.

In an embodiment, at least one of $R_1$, $R_2$ and $R_3$ is a C13 alkyl radical.

In an embodiment, at least one of $R_1$, $R_2$ and $R_3$ is a C14 alkyl radical.

In an embodiment, at least one of $R_1$, $R_2$ and $R_3$ is a C15 alkyl radical.

In an embodiment, at least one of $R_1$, $R_2$ and $R_3$ is a C16 alkyl radical.

In an embodiment, at least one of $R_1$, $R_2$ and $R_3$ is a C17 alkyl radical.

In an embodiment, at least one of $R_1$, $R_2$ and $R_3$ is a C18 alkyl radical.

In an embodiment, at least one of $R_1$, $R_2$ and $R_3$ is a C19 alkyl radical.

In an embodiment, at least one of $R_1$, $R_2$ and $R_3$ is a C20 alkyl radical.

In an embodiment, at least one of $R_1$, $R_2$ and $R_3$ is a C21 alkyl radical.

In an embodiment, at least one of $R_1$, $R_2$ and $R_3$ is a C22 alkyl radical.

In an embodiment, at least one of $R_1$, $R_2$ and $R_3$ is a C23 alkyl radical.

In an embodiment, at least one of $R_1$, $R_2$ and $R_3$ is a C24 alkyl radical.

In an embodiment, at least one of $R_1$, $R_2$ and $R_3$ is a C25 alkyl radical.

In an embodiment, at least one of $R_1$, $R_2$ and $R_3$ is a C26 alkyl radical.

In an embodiment, at least one of $R_1$, $R_2$ and $R_3$ is a C27 alkyl radical.

In an embodiment, at least one of $R_1$, $R_2$ and $R_3$ is a C28 alkyl radical.

In an embodiment, at least one of $R_1$, $R_2$ and $R_3$ is a C29 alkyl radical.

In an embodiment, at least one of $R_1$, $R_2$ and $R_3$ is a C30 alkyl radical.

In an embodiment, the at least branched alkane of formula II is obtained by dehydrogenation of a C24 to C48 Guerbet alcohol of general formula III, Formula III wherein $R_1$, $R_2$ and $R_3$ have the values defined above, followed by a hydrogenation.

In an embodiment, the at least C36 branched alkanes are obtained by dehydrogenation of Isofol 36 followed by a hydrogenation, to obtain 17-methylpentatriacontane. In an embodiment, the cosmetic ingredient can moreover comprise C18 to C28 alkanes of general formula I, obtained by dehydrogenation of alcohols originating from plant sources.

The dimerizations are carried out by a Guerbet reaction, starting from linear alcohols; alcohols branched in position 2 are obtained. The Guerbet reactions are run in the presence of hydroxides or metal alkoxides and Raney nickel catalysts at temperatures above 220° C. and under pressure. Reaction conditions such as those described in the patent US 2003/0181770 in the name of COGNIS can also be used.

The Guerbet alcohols or at least dimeric alcohols used can also be purchased, for example, from the company SASOL.

The dehydration reactions are run according to the conventional high-temperature methods in the presence of alumina or according to methods described, for example, in the patent application WO2010121591 in the name of SASOL. In another variant of the invention, the alkanes can be obtained from fatty alcohols by hydrogenolysis of the hydroxyl function, in the presence of hydrogen and of a metal catalyst.

The hydrogenation reactions are carried out by implementation of conventional catalysts such as nickel catalysts marketed by the company Johnson Matthey or by new-generation palladium catalysts, such as those described in the publication by R. Ciriminna et al., in Org. Process Res. Dev., 2014, 18(9), pp. 1110-1115.

The invention also relates to the use of the cosmetic ingredient according to the invention, in combination with a plant squalane, to yield a composition of which the organoleptic and sensory properties are preserved, while using less plant squalane.

It relates to the use of the cosmetic ingredient according to the invention, in combination with a plant squalane, for preparing a composition of which the organoleptic and sensory properties are preserved, while replacing at least 50% of plant squalane in the composition.

The invention also relates to a composition containing at most 50% plant squalane in combination with the cosmetic ingredient according to the invention.

The invention also relates to a composition comprising at most 50% plant squalane in combination with the cosmetic ingredient according to the invention.

The invention also relates to a composition comprising 30 to 50% plant squalane in combination with 50 to 70% of the cosmetic ingredient according to the invention.

EXAMPLES

I—General Conditions:
Dimerization Reaction:

The Guerbet reaction between two identical or different alcohols yields a mixture consisting of different isomers. This synthesis is carried out in the presence of a mixture of two alcohols, preferably in an equimolar ratio and in the presence of an alkaline base and of a catalyst based on copper oxide.

Dehydration Method:

The reactor used is a continuous tubular reactor which has the following characteristics:
Inner diameter: 12.5 mm
Total height: 370 mm
Height of the catalyst bed: 100 mm The catalyst bed is placed at mid-height of the reactor. A thermocouple is placed at the core of this bed. The latter is held by a grate on which silica wool is placed. Above the bed, silica wool is added, in order to immobilize the catalyst bed.

For this dehydration step, the catalyst used is an industrial alumina ($Al_2O_3$ 99%).

A weight of 6.436 g was loaded into the reactor, or a volume of 11.9 mL.

Hydrogenation Reactions

The hydrogenation reactions take place in a batch reactor having a capacity of one liter. The operating conditions are specified below.

The alkene and the catalyst (Raney nickel) are introduced into the reactor at ambient temperature. The reactor is rendered inert with 3×5 bar of nitrogen, and the temperature is raised to the working temperature of 180° C. 5 bar dihydrogen are then introduced. After two hours, the temperature is raised to 200° C. The reaction is then maintained for an additional 3 h.

II Obtention of the Alkanes in at Least Dimeric Form

II-1 Obtention of the C30 Alkanes in at Least Dimeric Form

Guerbet reaction between decanol and octyldodecanol (obtained by dimerization of decanol). The decanol is a fatty alcohol originating from the catalytic hydrogenation of coconut methyl esters.

The desired reaction between decanol and octyldodecanol yields a mixture of C30 isomers consisting mostly of trimers. See diagrams below. It can also give rise to the formation of C20 dimers originating from the reaction of decanol with itself.

The mixture of alcohols is then dehydrated according to the general conditions described above.

The mixture of alkenes obtained is then hydrogenated, yielding on average C30 trimeric alkanes, according to the invention.

| Consumption of dihydrogen per 1 ton of alkene, kg $H_2$ | Alkane formula (average) | Iodine alkene index g $I_2$/100 g | Alkane viscosity 40° C., mm$^2$/s | Alkane flow point, ° C. |
|---|---|---|---|---|
| 4.8 | C30H62 | <1 | 14 | −54 |

II-2 Obtention of the C32 Alkanes in at Least Dimeric Form

Guerbet reaction between dodecanol and octyldodecanol (obtained by dimerization of decanol). The dodecanol and decanol are fatty alcohols originating from the catalytic hydrogenation of coconut methyl esters.

The desired reaction between dodecanol and octyldodecanol yields a mixture of C32 isomers consisting primarily of trimers. It can also give rise to the formation of C24 dimers originating from the reaction of dodecanol with itself.

The mixture of alcohols is then dehydrated according to the general conditions described above.

The mixture of alkenes obtained is then hydrogenated, yielding on average C32 trimeric alkanes, according to the invention.

| Consumption of dihydrogen per 1 ton of alkene, kg $H_2$ | Alkane formula (average) | Iodine alkene index g $I_2$/100 g | Alkane viscosity 40° C., mm$^2$/s | Alkane flow point, ° C. |
|---|---|---|---|---|
| 4.5 | C32H66 | <1 | 16 | −30 |

II-3 Obtention of the C36 Alkanes in at Least Dimeric Form

Guerbet reaction between dodecanol and decatetradecanol (obtained by dimerization of dodecanol). The dodecanol is a fatty alcohol originating from the catalytic hydrogenation of coconut methyl esters.

The desired reaction between dodecanol and decatetradecanol yields a mixture of C36 isomers consisting primarily of trimers. It can also give rise to the formation of C24 dimers originating from the reaction of dodecanol with itself.

The mixture of alcohols is then dehydrated according to the general conditions described above.

The mixture of alkenes obtained is then hydrogenated, yielding on average C36 trimeric alkanes, according to the invention.

| Consumption of dihydrogen per 1 ton of alkene, kg $H_2$ | Alkane formula (average) | Iodine alkene index g $I_2$/100 g | Alkane viscosity 40° C., mm$^2$/s | Alkane flow point, ° C. |
|---|---|---|---|---|
| 4.0 | C36H74 | <1 | 20 | −24 |

III Examples of Synthesis of Branched Alkanes of General Formulas II:

III-1 Dehydration

The raw materials used are the following:

| Raw materials | Reference | Supplier |
|---|---|---|
| 2-decyltetradecanol | Isofol 24 | SASOL |
| 2-tetradecyloctadecanol | Isofol 32 | SASOL |
| 2-hexadecyleicosanol | Isofol 36 | SASOL |
| Alumina | | INDUSTRIAL 99% |
| Silica wool | | VWR |
| Nitrogen | Industrial | AIR LIQUIDE |

The LHSV (Liquid Hourly Space Velocity) corresponds to the flow rate of alcohol passing through the reactor, expressed in mL/min/mL of catalyst.

| | Dehydration results | | | | | |
|---|---|---|---|---|---|---|
| Alcohol | T, ° C. | LHSV | d (mL/min) | Conversion | Quantity of water produced per 1 ton of alcohol, kg | Quantity of alkene produced per 1 ton of alcohol, kg |
| Isofol 24 | 330 | 2.5 | 0.5 | >99% | 50.8 | 949.2 |
| Isofol 32 | 330 | 2.5 | 0.5 | >99% | 38.6 | 961.4 |
| Isofol 36 | 330 | 2.5 | 0 | >99% | 34.5 | 965.5 |

| Characterization of the alkenes | | |
|---|---|---|
| Alkene | Alkene formula | Iodine alkene index g $I_2$/100 g |
| Alkene iC24 | C24H48 | 75.5 |
| Alkene iC32 | C32H64 | 56.7 |
| Alkene iC36 | C36H72 | 50.4 |
| Plant squalene | C30H50 | 371.4 |
| Marine squalene | C30H50 | 371.4 |

III-2 Hydrogenation

According to the protocol described above, part I-3, the alkanes having the characteristics given in the table below are obtained.

| Characterization of the alkanes | | | | |
|---|---|---|---|---|
| Alkane | Consumption of hydrogen per 1 ton of alkene, kg H2 | Alkane formula | Viscosity 40° C. mm$^2$/s | Appearance at ambient temperature |
| Alkane i C24 | 6.0 | C24H50 | 8.0 | Liquid |
| Alkane i C32 | 4.5 | C32H66 | Nd | Solid |
| Alkane i C36 | 4.0 | C36H74 | nd | Solid |
| Plant squalane | 29.3 | C30H62 | 21.7 | Liquid |
| Marine squalane | 29.3 | C309H62 | 16.6 | Liquid |

IV—Examples of Compositions According to the Invention
Composition R

A composition according to the invention is prepared by mixing:
- 50% of olive squalane,
- 35% of C36 alkane in at least dimeric form,
- 10% of C30 alkane in at least dimeric form
- 5% of branched C32 alkane.

A composition which is non-greasy, fine and film-forming is obtained.

The stability is equivalent to that of shark squalane.

The viscosities at 40° C. in mm2/s and the refractive indexes are compared in the tables below and in FIGS. 1 and 2 with those of olive squalane, sugar cane squalane, shark squalane.

Figure 1:
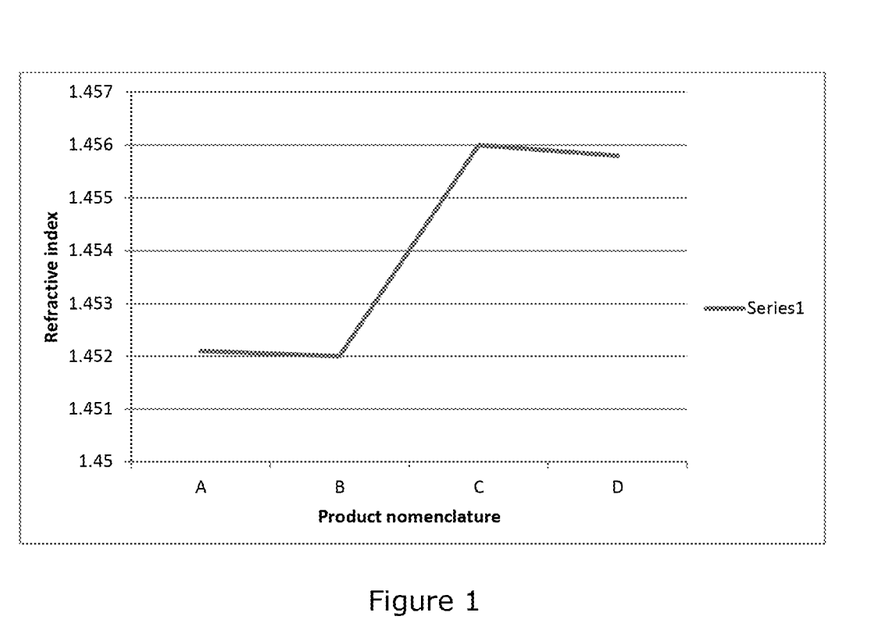
FIG. 1 is a graph showing the refractive index of the composition disclosed herein (D) as compared to the refractive indices of sugar cane squalane (A), shark squalane (B), and olive squalane (C).

Refractive Indexes (See FIG. 1)

| Product nomenclature | Product tested | Refractive index |
| --- | --- | --- |
| A | Sugar cane squalane | 1.4521 |
| B | Shark squalane | 1.4520 |
| C | Olive squalane | 1.4560 |
| D | Composition according to the invention | 1.4558 |

Figure 2:
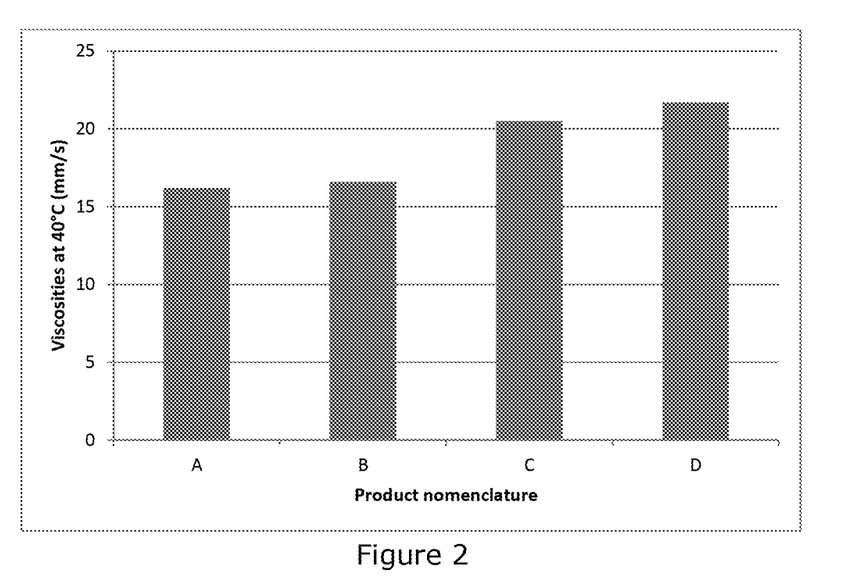
FIG. 2 is a chart showing the viscosity of the composition disclosed herein (D) as compared to the viscosities of sugar cane squalane (A), shark squalane (B), and olive squalane (C).

Viscosities at 40° C. in mm/s (See FIG. 2)

| Product nomenclature | Product tested | Viscosity at 40° C. in mm$^2$/s |
| --- | --- | --- |
| A | Sugar cane squalane | 16.2 |
| B | Shark squalane | 16.6 |
| C | Olive squalane | 20.5 |
| D | Composition according to the invention | 21.7 |

In conclusion, the viscosities and the refractive indexes of the composition according to the invention are equivalent to those of olive squalane.

Composition S

A composition according to the invention is prepared by mixing:
- 30% of olive squalane,
- 17.5% of C24 alkane in at least dimeric form,
- 52.5% of C36 alkane in at least dimeric form, Composition T A composition according to the invention is prepared by mixing:
- 50% of olive squalane,
- 10% of C20 alkane in at least dimeric form,
- 40% of C36 alkane in at least dimeric form, V—Characterization of the Compositions According to the Invention by Texturometry A test reproducing the sensory characteristics was carried out, and the consistency, the cohesion, the firmness and tackiness were characterized for compositions according to the invention and squalanes.

The protocols used are described in the thesis by Laura Gilbert. Caractérisation physico-chimique et sensorielle d'ingrédients cosmétiques: une approche méthodologique [Physicochemical and sensory characterization of cosmetic ingredients: a methodological approach]. Polymers. University of Havre, 2012, in particular pages 126 and 127, and in the publication by Laura Gilbert in 2 Colloids and surfaces A: Physicochem. Eng. Aspects 421 (2013) 150-163, page 152, paragraph 2.2.3.

The apparatus used is a TA.XT Plus texturometer.

In FIGS. 3, 4, 5 and 6, the results pertaining to the following compositions or ingredients have been collected:
- Product 1: Sugarcane squalane Neossance
- Product 2: Plantasens OLIVE Squalane from Clariant
- Product 3: Olive squalane (Squalive) Biosynthis
- Product 4: 50% mixture of C20 to C36 alkanes+50% Olive squalane (Squalive) Biosynthis (composition S)
- Product 5: 70% mixture of C24 to C36 alkanes+30% Olive squalane (Squalive) Biosynthis (composition r)

Figure 3:
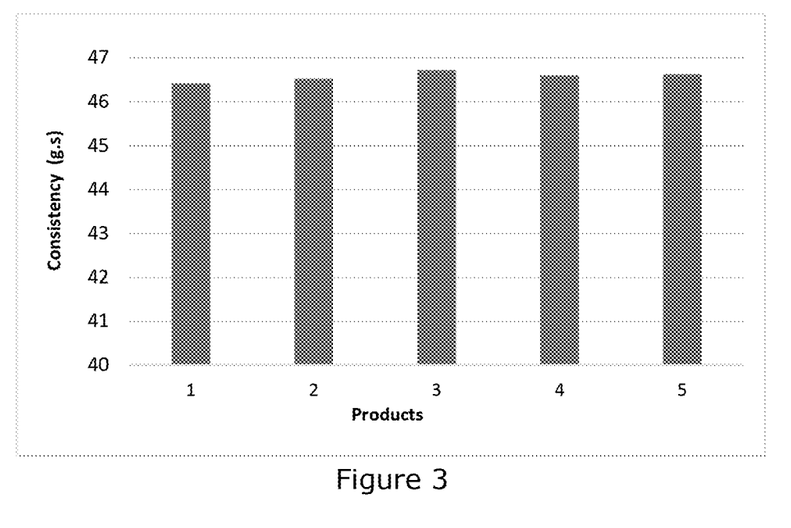
FIG. 3 is a chart showing the consistency in g.s. of Product 1: Sugarcane squalane Neossance; Product 2: Plantasens OLIVE Squalane from Clariant; Product 3: Olive squalane (Squalive) Biosynthis; Product 4: 50% mixture of C20 to C36 alkanes+50% Olive squalane (Squalive) Biosynthis (composition S); and Product 5: 70% mixture of C24 to C36 alkanes+30% Olive squalane (Squalive) Biosynthis (composition r).

FIG. 3 represents the results obtained for consistency in g.s. The results are subjected to a variance analysis (ANOVA), and no significant difference between the different products tested is observed.

Figure 4:
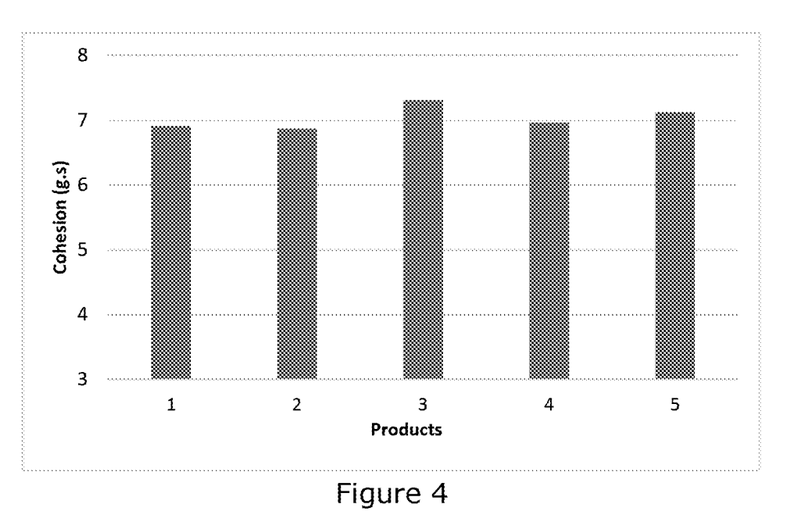
FIG. 4 is a chart showing the cohesion in g.s. of Product 1: Sugarcane squalane Neossance; Product 2: Plantasens OLIVE Squalane from Clariant; Product 3: Olive squalane (Squalive) Biosynthis; Product 4: 50% mixture of C20 to C36 alkanes+50% Olive squalane (Squalive) Biosynthis (composition S); and Product 5: 70% mixture of C24 to C36 alkanes+30% Olive squalane (Squalive) Biosynthis (composition r).

FIG. 4 represents the results obtained for cohesion in g.s. The results are subjected to a variance analysis (ANOVA), and no significant difference between the different products tested is observed.

Figure 5:
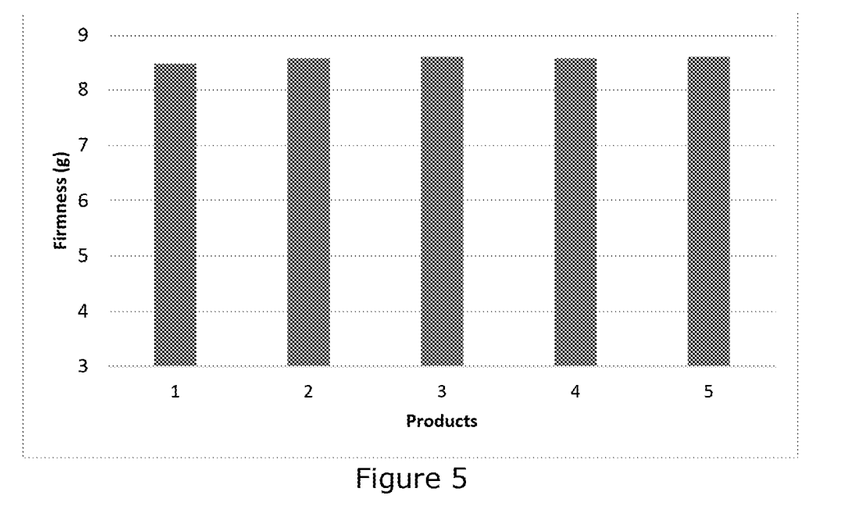
FIG. 5 is a chart showing the firmness in g. of Product 1: Sugarcane squalane Neossance; Product 2: Plantasens OLIVE Squalane from Clariant; Product 3: Olive squalane (Squalive) Biosynthis; Product 4: 50% mixture of C20 to C36 alkanes+50% Olive squalane (Squalive) Biosynthis (composition S); and Product 5: 70% mixture of C24 to C36 alkanes+30% Olive squalane (Squalive) Biosynthis (composition r).

FIG. 5 represents the results obtained for firmness in g. The results are subjected to a variance analysis (ANOVA), and no significant difference between the different products tested is observed.

Figure 6:
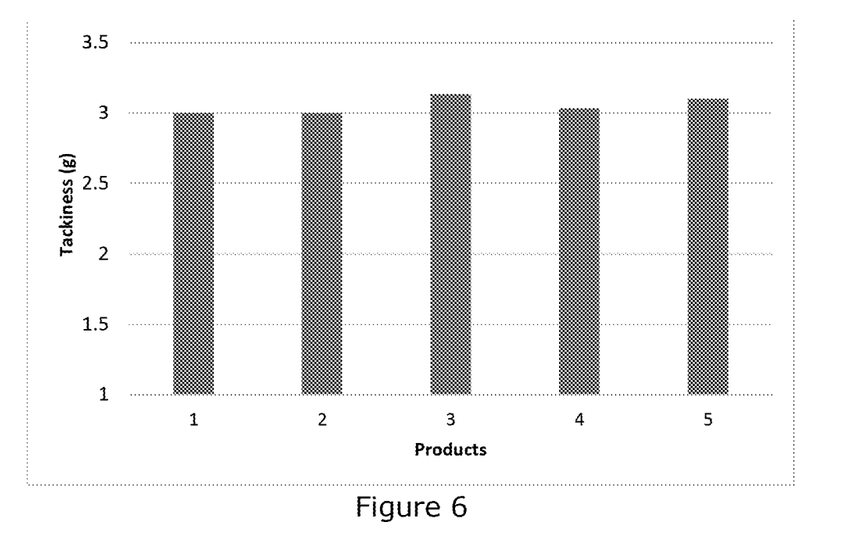
FIG. 6 is a chart showing tackiness in g. of Product 1: Sugarcane squalane Neossance; Product 2: Plantasens OLIVE Squalane from Clariant; Product 3: Olive squalane (Squalive) Biosynthis; Product 4: 50% mixture of C20 to C36 alkanes+50% Olive squalane (Squalive) Biosynthis (composition S); and Product 5: 70% mixture of C24 to C36 alkanes+30% Olive squalane (Squalive) Biosynthis (composition r).

FIG. 6 represents the results obtained for tackiness in g. The results are subjected to a variance analysis (ANOVA), and no significant difference between the different products tested is observed.

VI—Characterization of the Compositions According to the Invention by Goniometry Compositions according to the invention and squalanes were characterized by goniometry according to the protocol described in the publication by G. Savary in Colloids and surfaces Biointerfaces 102 (2013) 371-378, on page 372, paragraph 2.2.1.

The apparatus used is a Digidrop GBX.

Figure 7:
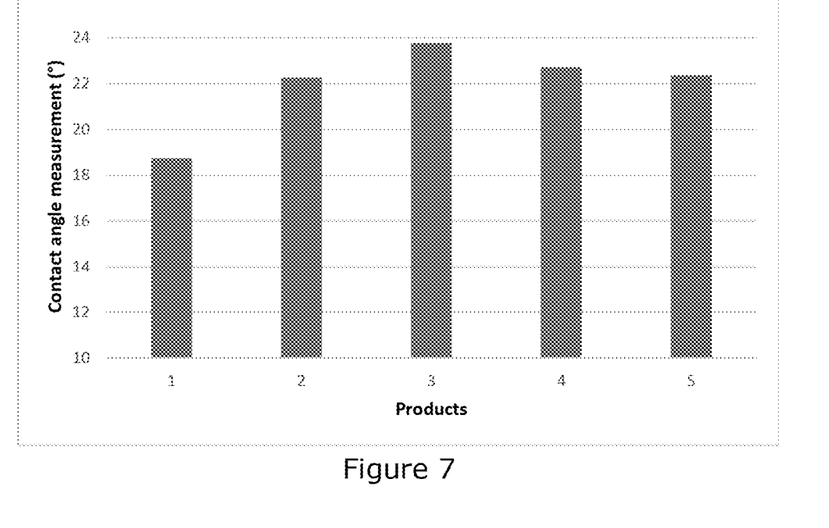
FIG. 7 is a chart showing the contact angle measurements after 1 s for Product 1: Sugarcane squalane Neossance; Product 2: Plantasens OLIVE Squalane from Clariant; Product 3: Coconut squalane (Squalive) Biosynthis; Product 4: 50% mixture of C24 to C48 alkanes+50% Coconut squalane (Squalive) Biosynthis; and Product 5: 70% mixture of C24 to C48 alkanes+30% Coconut squalane (Squalive) Biosynthis.
Figure 8:
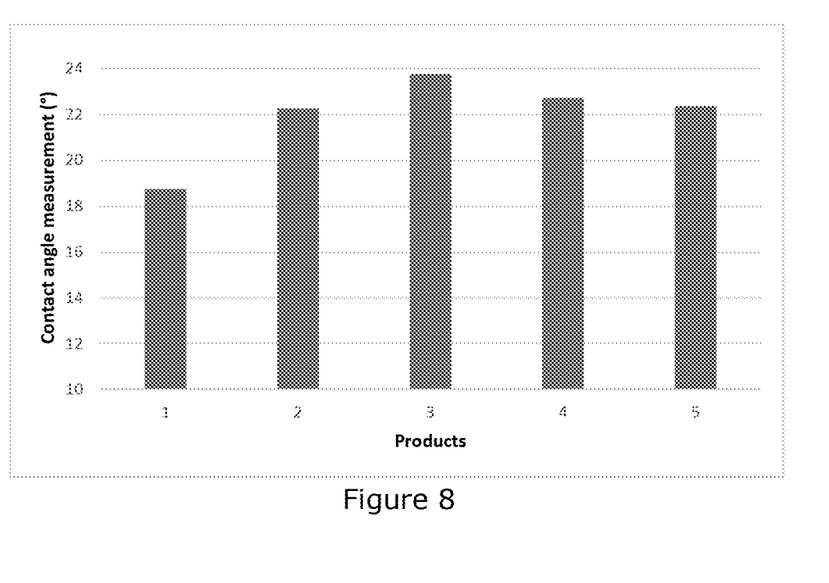
FIG. 8 is a chart showing the contact angle measurements after 4 s for Product 1: Sugarcane squalane Neossance; Product 2: Plantasens OLIVE Squalane from Clariant; Product 3: Coconut squalane (Squalive) Biosynthis; Product 4: 50% mixture of C24 to C48 alkanes+50% Coconut squalane (Squalive) Biosynthis; and Product 5: 70% mixture of C24 to C48 alkanes+30% Coconut squalane (Squalive) Biosynthis.

In FIGS. 7 and 8, the results pertaining to the following compositions or ingredients have been collected:
- Product 1: Sugarcane squalane Neossance
- Product 2: Plantasens OLIVE Squalane from Clariant
- Product 3: Coconut squalane (Squalive) Biosynthis
- Product 4: 50% mixture of C24 to C48 alkanes+50% Coconut squalane (Squalive) Biosynthis
- Product 5: 70% mixture of C24 to C48 alkanes+30% Coconut squalane (Squalive) Biosynthis The results are expressed in degree ° and subjected to a variance analysis (ANOVA)

The results presented in FIG. 7 are contact angle measurements after 1 s.

The results presented in FIG. 8 are contact angle measurements after 4 s.

V—Cosmetic Formulations Comprising Compositions According to the Invention

Make-Up Foundation Composition:

| | Phase A: | |
| --- | --- | --- |
| INCI | Ingredients | wt %/total weight |
| Abil EM 90 | Cetyl PEG/PPG-10/1 dimethicone | 2.80 |
| | Phenyl trimethicone | 1 |
| | Composition according to the invention S | 3 |
| | Cetearyl ethylhexanoate | 2 |
| Vegelight 1214 | Plant hydrocarbons | 1.8 |

-continued

| Ingredients | wt %/total weight |
|---|---|
| Phase B: | |
| Mica | 0.5 |
| Red oxide and dimethicone | 0.22 |
| Yellow oxide and dimethicone | 0.75 |
| Black iron oxide and dimethicone | 0.12 |
| Titanium oxide and dimethicone | 8.5 |
| Phase C | |
| Sodium chloride | 1.25 |
| Phenoxyethanol | 0.50 |
| Butylene glycol | 5.00 |
| Water | Sufficient quantity for 100 |
| Perfume | sufficient quantity |

Dry Oil Composition

| Ingredients | INCI | wt %/total weight |
|---|---|---|
| Phase A: | | |
| Caprylic/capric triglyceride | Neoderm MCT | 10.00 |
| *Simmondsia chinensis* | Organic Jojoba oil | 5.00 |
| Composition according to the invention S | | 59.9 |
| Phase B: | | |
| Plant hydrocarbons | VEGELIGHT 1214 | 20.00 |
| Perfume | | sufficient quantity |

The invention claimed is:

1. A cosmetic ingredient comprising at least one plant squalane and at least one mixture of C24 to C48 alkanes, chosen amongst the alkanes of formula I, Formula I wherein
n is equal to 0,
$R_1$, $R'_1$, and $R_2$ are each a hydrogen atom —H, $R'_2$ is a methyl radical, and $R_3$ and $R'_3$ are chosen amongst linear C8 to C30 alkyl radicals, and
said mixture of C24 to C48 alkanes has a viscosity between 12 and 25 mm²/s at 40° C.

2. The ingredient according to claim 1, wherein the alkanes of formula I are a mixture of C30 to C36 alkanes.

3. The ingredient according to claim 1, further comprising at least one branched C24 to C48 alkane of general formula II, Formula II wherein
$R_1$, $R_2$ and $R_3$, which may be identical or different, are chosen amongst linear C8 to C30 alkyl radicals and a hydrogen atom, and
at most one of $R_1$, $R_2$ and $R_3$ is a hydrogen atom.

4. The ingredient according to claim 3, wherein the at least one branched alkane of formula II is a C28 to C36 alkane.

5. The ingredient according to claim 3, wherein all of $R_1$, $R_2$, and $R_3$ in Formula II, which may be identical or different, are chosen amongst the linear C8 to C30 alkyl radicals.

6. The ingredient according to claim 1, wherein the at least one plant squalane is olive squalane.

7. A method comprising combining the cosmetic ingredient according to claim 1 with an additional plant squalane to yield a composition containing at most 50% of the additional plant squalane.

8. A cosmetic ingredient comprising at least one plant squalane and at least one mixture of C24 to C48 alkanes, in at least dimeric form, chosen amongst the alkanes of formula I, Formula I wherein
$R'_1$ and $R_1$ are each a hydrogen atom,
n is equal to 0, and
$R_2$, $R'_2$, $R_3$ and $R'_3$ are chosen amongst linear C8 to C30 alkyl radicals and at least one and at most one of $R_2$, $R'_2$, $R_3$ and $R'_3$ is a methyl radical.

9. A cosmetic ingredient comprising:
at least one plant squalane, and
at least one mixture of C24 to C48 alkanes, in at least dimeric form, chosen amongst the alkanes of Formula I, Formula I wherein
n is equal to 0,
$R_1$, $R'_1$, $R_2$, $R'_2$, $R_3$ and $R'_3$, which may be identical or different, are chosen amongst the group consisting of a hydrogen atom —H, a methyl radical, and linear C8 to C30 alkyl radicals,
at least one of $R_1$, $R'_1$, $R_2$, $R'_2$, $R_3$ and $R'_3$, which may be identical or different, is chosen amongst the linear C8 to C30 alkyl radicals, and
at least one and at most one of $R_1$, $R'_1$, $R_2$, $R'_2$, $R_3$ and $R'_3$ is a methyl radical, said mixture of C24 to C48 alkanes having a viscosity between 12 and 25 mm²/s at 40° C.

10. The ingredient according to claim 9, wherein the alkanes of formula I are a mixture of C30 to C36 alkanes.

11. The ingredient according to claim 9, further comprising at least one branched C24 to C48 alkane of general formula II, Formula II wherein
at most one of $R_1$, $R_2$ and $R_3$ is a hydrogen atom,
R1, R2 and R3, which may be identical or different, are chosen amongst linear C8 to C30 alkyl radicals and a hydrogen atom, and
at most one of R1, R2 and R3 is a hydrogen atom.

12. The ingredient according to claim 11, wherein the at least one branched alkane of formula II is a C28 to C36 alkane.

13. The ingredient according to claim 11, wherein all of $R_1$, $R_2$, and $R_3$ in Formula II, which may be identical or different, are chosen amongst the linear C8 to C30 alkyl radicals.

14. The ingredient according to claim 9, wherein the at least one plant squalane is olive squalane.

15. A method comprising combining the cosmetic ingredient according to claim 9 with an additional plant squalane to yield a composition containing at most 50% of the additional plant squalane.

* * * * *